United States Patent [19]
Scott et al.

[11] Patent Number: 6,160,188
[45] Date of Patent: Dec. 12, 2000

[54] HYDROGENATION CATALYST AND PROCESS

[75] Inventors: John David Scott, Cuddington; Gary Goodyear, Wirral; John Charles McCarthy, Warrington, all of United Kingdom

[73] Assignee: Imperial Chemical Industries PLC, London, United Kingdom

[21] Appl. No.: 09/101,529

[22] PCT Filed: Dec. 12, 1996

[86] PCT No.: PCT/GB96/03067

§ 371 Date: Jul. 10, 1998

§ 102(e) Date: Jul. 10, 1998

[87] PCT Pub. No.: WO97/25142

PCT Pub. Date: Jul. 17, 1997

[30] Foreign Application Priority Data

Jan. 10, 1996 [GB] United Kingdom .................. 9600430

[51] Int. Cl.⁷ .................................................. C07C 17/354
[52] U.S. Cl. ........................................... 570/176; 502/330
[58] Field of Search .............................. 502/330; 570/176

[56] References Cited

U.S. PATENT DOCUMENTS

| | | | |
|---|---|---|---|
| 4,199,436 | 4/1980 | Courty | 502/330 X |
| 4,496,666 | 1/1985 | Frederick et al. | |
| 5,053,377 | 10/1991 | Lerot et al. | 502/330 X |
| 5,561,096 | 10/1996 | Schoebrechts et al. | 502/330 |

FOREIGN PATENT DOCUMENTS

| | | |
|---|---|---|
| 0 133 778 | 3/1985 | European Pat. Off. . |
| 0 355 907 | 2/1990 | European Pat. Off. . |
| 0 508 660 | 10/1992 | European Pat. Off. . |
| 0 657 413 | 6/1995 | European Pat. Off. . |
| 0 669 304 | 8/1995 | European Pat. Off. . |

*Primary Examiner*—Michael G. Ambrose
*Attorney, Agent, or Firm*—Cook, Alex, McFarron, Manzo, Cummings & Mehler, Ltd.

[57] ABSTRACT

A process for the production of a hydrofluoroalkane is disclosed which comprises contacting a halofluorocarbon or hydrohalofluorocarbon with hydrogen at elevated temperature in the presence of a hydrogenation catalyst which comprises palladium and an alkali metal carried on a support.

15 Claims, No Drawings

HYDROGENATION CATALYST AND PROCESS

This invention relates to a hydrogenation catalyst and to a hydrogenation processes employing the catalyst. The term "hydrogenation" as used herein means all reactions of starting materials with hydrogen and includes hydrogenolysis reactions (replacement of halogen by hydrogen in saturated molecules) as well as hydrogenation reactions (addition of hydrogen across ethylenic double bonds). In a particular embodiment the invention relates to a catalyst and a process for the hydrogenation of halofluorocarbons and hydrohalofluorocarbons to produce hydrofluoroalkanes, for example hydrogenation of dichlorodifluoromethane and chlorodifluoromethane to produce difluoromethane, hydrogenation of chiloropentafluoroethane to produce pentafluoroethane and hydrogenation of dichlorotetrafluoroethane and chlorotetrafluoroethane to produce tetrafluoroethane especially 1,1,1,2-tetrafluoroethane.

Hydrofluorocarbons (HFCs) such as difluoromethane, also known as HFA 32, pentafluoroethane, also known as HFA 125 and 1,1,1,2-tetrafluoroethane, also known as HFA 134a are of interest as replacements for chlorofluorocarbons (CFCs) in the many applications in which CFCs have hitherto been used and in particular in refrigeration and air-conditioning applications. Hydrochlorofluorocarbons (HCFCs) are also of interest as at least transitional replacements for CFCs Many processes have been proposed for the production of hydrofluorocarbons and hydrochlorofluorocarbons, including the catalysed gas phase hydrofluorination of halocarbons and hydrohalocarbons and the catalysed hydrogenation of halocarbons and hydrohalocarbons which contain fluorine. The catalysed hydrogenation of chlorofluorocarbons and hydrohalofluorocarbons by reaction with hydrogen in the presence of a hydrogenation catalyst is considered to be a potentially commercially attractive process. Hydrogenation of dichlorotetrafluoroethane and chlorotetrafluoroethane to 1,1,1,2-tetrafluoroethane is described, for example, in UK Patent No. 1,578,933; hydrogenation of chloropentafluoroethane to pentafluoroethane has been described, for example, in Japanese Laid-Open Patent Application No. J4-29941; hydrogenation of chlorodifluoromethane to difluoromethane is described, for example, in European Patent Publication No. 0 508 660.

Hydrogenation catalysts for use in the production of HFCs and usually comprising palladium carried on a support such as carbon or alumina are well known and much attention has been directed towards improving such catalysts to increase the activity of the catalyst and/or especially to increase the selectivity with which the desired HFA product is produced using the catlayst. Thus, catalysts for use in the hydrogenation of chlorofluorocarbons and hydrochlorofluorocarbons have been disclosed, inter alia, in International Patent Publications Nos. WO90/08748, WO92/12113 and WO94/11328, US Pat. No. 5,136,113, European Patent Application No. 0 347 830 and Japanese Kokai No. J4-179322.

The present invention is based on the improvement of palladium-based catalysts and in particular on improvement of the selectivity of such catalysts by incorporating an alkali metal such as potassium in the catalysts.

According to the present invention there is provided a catalyst which comprises palladium and an alkali metal carried on a support.

Any alkali metal may be used as a component of the catalyst although caesium or potassium is preferred, especially potassium.

The palladium and alkali metal components may be used in combination with other metals, for example other Group VIII metals such as nickel, Group IB metals such as silver and gold or other metals.

The metals are carried on a suitable support, for example alumina, fluorinated alumina, silica, silicon carbide or carbon but in particular alumina or carbon. We particularly prefer to employ a carbon having a high surface area for example greater than 200 $m^2/gm$. Activated carbon supports with low inorganic impurity levels are particularly suitable.

The loading of the metals on the support material may be dependent at least to some extent on the particular metal/support combination being used and the difficulty of the hydrogenation reaction to be performed. However, the % w/w of combined palladium and alkali metal in the catalyst is typically from about 0.1% w/w to about 40% w/w, preferably from about 0.5% w/w to about 20% w/w. We especially prefer a loading of at least 1% w/w of the catalyst, more preferably from about 2.0% w/w to about 20% w/w and especially from about 2% w/w to about 15% w/w.

The proportions of palladium and alkali metal in the catalyst may vary within a wide range although generally we prefer to employ a catalyst which is based on palladium (i.e. in which on a % w/w basis palladium is the major component) and in particular in which there is at least twice as much palladium present as alkali metal. We particularly prefer to employ palladium and alkali metal in the ratio by weight of from about 2:1 to about 500:1 and more preferably from about 3:1 to about 100:1. A preferred catalyst comprises from about 0.5% to 20%, in particular from about 5 to 15% w/w palladium and from about 0.05% to about 5%, in particular from about 0.1% to about 4% by weight alkali metal, especially when supported on an active carbon. Overall the amount of alkali metal is usually in the range from about 0.01% w/w to about 10% w/w.

Many methods for the preparation of supported metal hydrogenation catalysts are known to those skilled in the art, for example as described in the documents referred to herein and the improved catalyst of the invention may be prepared by any such method. A typical method involves impregnating the support with an aqueous solution of the salts, usually the chloride salts, of the metals and thereafter drying the catalyst.

The catalyst of the invention is particularly useful in the hydrogenation of a halofluorocarbon or hydrohalofluorocarbon in the gas phase at elevated temperature and according to the present invention there is also provided a process for the production of a hydrofluoroalkane which comprises contacting a halofluorocarbon or hydrohalofluorocarbon with hydrogen at elevated temperature in the presence of a hydrogenation catalyst as herein defined.

Usually the halofluorocarbon and hydrohalofluorocarbon used as starting material will comprise at least one atom of chlorine or bromine and generally will be a chlorofluorocarbon or a hydrochlorofluorocarbon. The chlorofluorocarbon or hydrochlorofluorocarbon will typically comprise 1, 2 or 3 carbon atoms although it may comprise more than 3, say up to 6, carbon atoms. The (hydro)halofluorocarbon may be unsaturated or saturated, cyclic or acyclic and straight chain or branched chain, although it will usually be a straight chain saturated acyclic compound, that is a linear (hydro) halofluoroalkane.

Particularly useful hydrogenation reactions in which the catalyst may be employed include (a) the hydrogenation of a haloethane having 4 fluorine atoms, for example 1,1-dichlorotetrafluoroethane, 1,2-dichlorotetrafluoroethane and chlorotetrafluoroethane to chlorotetrafluoroethane and/or tetrafluoroethane, in particular 1,1,1,2-tetrafluoroethane (b) the hydrogenation of a compound of formula $CF_2XY$ where X and Y are independently Cl, Br or H (but not both H) to difluoromethane and (c) the hydrogenation of chloropentafluoroethane to pentafluoroethane.

Conditions for effecting the hydrogenation reactions are described, for example, in UK Patent Specification No. 1,578,933 and European Patent Application No. 0 508 660, the disclosures of which are incorporated herein by reference. An important feature of successful hydrogenation catalysts is a high hydrogenolysis activity for carbon-chlorine and/or carbon-bromine bonds but a low hydrogenolysis activity for carbon-fluorine bonds thereby avoiding loss of desired product by removal of fluorine atoms.

Use of the catalyst of the invention in the production of hydrofluoroalkanes affords an enhancement of the selectivity with which the hydrofluoroalkanes are produced. A significant enhancement in selectivity is afforded when the catalyst is employed in the production of difluoromethane by hydrogenation of chlorodifluoromethane and/or dichlorodifluoromethane.

According to a particular embodiment of the invention there is provided a process for the production of difluoromethane which comprises reacting a compound of formula $XYCF_2$ wherein X and Y are each H, Cl or Br but at least one of X and Y is an atom other than hydrogen with hydrogen at elevated temperature in the presence of a hydrogenation catalyst as herein defined.

The process may be conveniently effected by feeding the compound of formula $XYCF_2$ and hydrogen as a combined stream or as separate streams through a vessel containing the hydrogenation catalyst which may be in the form of a fixed bed or a fluid bed.

The starting compounds of formula $XYCF_2$ are dichlorodifluoromethane, dibromodifluoromethane, chlorobromodifluoromethane, chlorodifluoromethane and bromodifluoromethane. Mixtures of the above compounds may be employed. Usually the compound of formula $XYCF_2$ will be a chlorinated difluoromethane and chlorodifluoromethane is the preferred starting compound.

The proportion of hydrogen to starting compound of formula $XYCF_2$ may be varied considerably but usually at least the stoichiometric amount of hydrogen will be employed to replace all the chlorine and/or bromine atom(s) in the starting compound. Greater than stoichiometric amounts of hydrogen, for example 4 or more moles of hydrogen per mole of starting compound may be employed. Where X and Y are each chlorine or bromine, it is preferred to employ more than two moles of hydrogen (the stoichiometric amount) per mole of starting compound. Where the starting compound of formula $XYCF_2$ is chlorodifluoromethane it is preferred to employ between 1 (the stoichiometric amount) and 2 moles of hydrogen per mole of chlorodifluoromethane.

Atmospheric or superatmospheric pressure for example up to about 60 barg may be employed. We have found that operation of the process of the invention at superatmospheric pressure substantially increases the selectivity of the process towards the production of difluoromethane. The process is preferably operated at a pressure in the range from about 2 bar to about 60 bar and more preferably from about 2 bar to about 30 bar, especially 5 bar to 20 bar.

The reaction is suitably carried out in the vapour phase at a temperature which is at least 150° C. and not greater than about 500° C., usually from about 225° C. to about 450° C., and preferably from about 240° C. to about 400° C. The optimum temperature is dependent upon the pressure at which the process is operated; at atmospheric pressure we prefer to operate at a temperature in the range from about 220° C. to about 320° C. whilst at a pressure of about 7.5 bar we prefer to employ temperatures in the range from about 260° C. to about 380° C.

Contact times are usually in the range 1 to 60 seconds, especially 5 to 30 seconds, when the reaction is carried out in the vapour phase.

Suitably the desired product is separated from the process stream, for example by conventional means. Other components in the process stream may then be recycled to the process at a point upstream of the separation step as desired. For example, any unreacted hydrogen, other starting material and organic by-products or combination thereof, may be recycled after separaton of the desired product.

The invention is illustrated but not limited by the following examples.

A. CATALYST PREPARATION.

A sample of carbon support (supplied by Norrit) with an approximate surface area area of 800 sq.m/g was taken and crushed and sieved to generate particles in the size range 1.0–1.2 mm. 50 cm³–60 cm³ of the crushed carbon was then washed in distilled water and the water drained through a no. 4 sinter funnel. The washed carbon was then transferred to a Buchner flask. The target weight of palladium chloride or mixed metal chlorides was then dissolved in the minimum volume of warmed concentrated hydrochloric acid and the solution was added to the carbon particles in the Buchner flask. A further 200 cm³ of distilled water was then added to the flask and the slurry was evaporated to dryness on a rotary evaporator, using an oil bath temperature of 120° C. The catalyst was finished by heating the granules in a vacuum oven at 150° C. for approximately 16 hours.

B. CATALYSTS TESTING.

50 cm³ of the finished catalyst to be tested was charged to a ½" Inconel reactor and heated to 300° C. in a nitrogen stream of 300 cm³/min. After the catalyst had been dried for 2 hours, the nitrogen flow was replaced with a stream of mixed reactant gases. A mixed reactant flow rate of 180 cm³/min was employed with a hydrogen:chlorodifluoromethane molar ratio of 2:1. The reactor vent gases were scrubbed to remove acid products and then analysed using conventional gas chromatographic analysis. The catalyst performance was determined for reactor temperatures in the range of 260–380° C. as shown in the Table.

Five catalysts were prepared and tested, and the results (% selectivity to difluoromethane) are shown in the Table.

TABLE

SELECTIVITY (%) TO DIFLUOROMETHANE

| Temp. °C. | Catalyst | | | | |
|---|---|---|---|---|---|
| | 10% Pd | 10% Pd 3.6% K | 10% Pd 0.36% K | 13% Pd | 13% Pd 0.4% K |
| 260 | | | | | 95.4 |
| 280 | | | | 92.8 | 94 |
| 300 | 87 | 87.5 | 87.3 | 92.9 | 93.4 |
| 320 | 87.8 | | 90 | | |
| 340 | 85.8 | 90.5 | 90.1 | 92 | 94.4 |
| 360 | 86.1 | 86.7 | 86.1 | | |
| 380 | 85 | 88.1 | 84.5 | | 94 |

The results show that adding potassium to the palladium catalyst increases the selectivity of the process to difluoromethane as also does increasing the palladium loading in the catalyst.

What is claimed is:

1. A process for the production of a hydrofluoroalkane which comprises contacting a halofluorocarbon or hydrohalofluorocarbon with hydrogen at elevated temperature in the presence of a hydrogenation catalyst which comprises palladium and an alkali metal carried on a support.

2. A process for the production of difluoromethane which comprises reacting a compound of formula $XYCF_2$, wherein X and Y are each H, Cl or Br, but at least one of X and Y is an atom other than H, with hydrogen at elevated temperature in the presence of a hydrogenation catalyst which comprises palladium and an alkali metal carried on a support.

3. A process as claimed in claims 1 or 2 in which the total amount of palladium and alkali metal is from 0.1 to 40% w/w of the catalyst.

4. A process as claimed in claims 1 or 2 in which the % w/w of palladium exceeds the % w/w of alkali metal.

5. A process as claimed in claims 1 or 2 in which the ratio by weight of palladium to alkali metal is from 2:1 to 500:1.

6. A process as claimed in claims 1 or 2 which comprises from 0.5 to 20% by weight palladium and from 0.05 to 5% by weight of alkali metal.

7. A process as claimed in claims 1 or 2 in which the alkali metal is potassium.

8. A process as claimed in claim 1 or 2 in which at least the stoichiometric equivalent of hydrogen is employed to replace the non-fluorine halogen atoms in the halofluorocarbon or hydrohalofluorocarbon.

9. A process as claimed in claim 1 or 2 which is carried out at elevated pressure.

10. A process as claimed in claim 9 in which the pressure is from 2 to 60 barg.

11. A process as claimed in claim 1 or 2 which is carried out at a temperature of 150 to 500° C.

12. A process as claimed in claim 1 or 2 in which the desired product is separated from the process stream and at least one other component of the process stream is recycled to a point upstream of the said product separation.

13. A process as claimed in claim 12 in which the said at least one other component is selected from unreacted hydrogen, other unreacted starting material and organic by-products.

14. A process of using a hydrogenation catalyst which comprises palladium and an alkali metal carried on a support in a process for the production of a hydrofluoroalkane which process comprises contacting a halofluorocarbon or hydrohalofluorocarbon with hydrogen at elevated temperature in the presence of said catalyst.

15. A process of using a hydrogenation catalyst which comprises palladium and an alkali metal carried on a support in a process for the production of difluoromethane which comprises reacting a compound of the formula $XYCF_2$, wherein X and Y are each H, Cl or Br, but at least one of X and Y is an atom other than H, with hydrogen at elevated temperature in the presence of said catalyst.

* * * * *